United States Patent [19]

Renga et al.

[11] Patent Number: 4,959,488

[45] Date of Patent: Sep. 25, 1990

[54] POLYFUNCTIONAL HEXASUBSTITUTED BENZENE DERIVATIVES

[75] Inventors: James M. Renga; Alan G. Olivero; Mark Bosse, all of Santa Rosa, Calif.

[73] Assignee: Henkel Research Corporation, Santa Rosa, Calif.

[21] Appl. No.: 353,371

[22] Filed: May 17, 1989

[51] Int. Cl.$^5$ .................... C07C 69/773; C07C 57/30; C07C 33/26; C07C 67/30

[52] U.S. Cl. ...................... 560/76; 556/489; 558/24; 558/46; 558/61; 558/62; 558/155; 558/156; 558/388; 560/81; 560/96; 560/254; 562/480; 562/489; 564/82; 564/153; 564/374; 564/381; 564/391; 568/17; 568/25; 568/28; 568/29; 568/39; 568/50; 568/57; 568/811

[58] Field of Search ............... 560/76, 81, 96, 254; 562/480, 489; 68/811, 17, 25, 28, 29, 39, 50, 57; 558/24, 46, 61, 62, 155, 156, 388; 556/489; 564/82, 153, 374, 381, 391

[56] References Cited

U.S. PATENT DOCUMENTS 3,362,984  1/1968  Chini et al. ........................... 560/76
4,578,210  3/1986  Praefeke et al. .................. 560/76 X
4,734,522  3/1988  Praefeke et al. ................ 560/187 X

OTHER PUBLICATIONS

Chemistry and Industry, Reactions of Acetylenes on Noble Metal Catalysts in the Absence of Hydrogen, 2/8/64, D. Bryce-Smith, p. 239.
Journal Chemie., Darstellung und Eigenschaften Hexasubstituierter Benzenderivate (1986), Rosenthal et al., pp. 335–341.
Chem. Ben., Die Cyclisierende Trimerisierung von Alkinen mit Hilfe von Metallcarbonyl-Verbingungen, 1960, Hübel et al., pp. 103–115.
C. R. Hebd. Seancas. Acad. Science, 1866, pp. 905–909.
Liebigs Ann. Chem., 560, Cyclisierende Polymerisation von Acetylen. III, 4/19/48, Reppe et al., pp. 104–116.
J. C. S. Dalton Trans., 1981, Booth et al., pp. 2593–2595.
J.A.C.S., Reactions of Acetylenes with Noble-Metal Halides, 4/22/70, Dietl et al., pp. 2276–2285.
J. Org. Chem., 52, Homogeneous Catalysis with a Hetyerogeneous Pd Catalyst, 1987, Jhingan et al., pp. 1161–1165.

*Primary Examiner*—Werren B. Lone
*Assistant Examiner*—Vera C. Clarke
*Attorney, Agent, or Firm*—Ernest G. Szoke; Wayne C. Jaeschke; John E. Draoh

[57] ABSTRACT

Polyfunctional hexasubstituted benzene derivatives wherein at least three of the substituents are saturated carbon chains having from 1 to 21 carbon atoms and functional groups containing hetero functionalities at the ends of the carbon chains and the remainder of the 6 substituents are either saturated carbon chains containing from 1 to 21 carbon atoms or saturated carbon chains containing from 1 to 21 carbon atoms having a functional group including a hetero functional group containing N, O, S, P, or Si at the end of the chains. These derivatives are made by reacting a disubstituted alkyne wherein one or both of the substituents are saturated carbon chains having 1 to 21 carbon atoms to which hetero functional groups are attached with a palladium catalyst and isolating the resulting hexasubstituted benzene derivative.

31 Claims, No Drawings

POLYFUNCTIONAL HEXASUBSTITUTED BENZENE DERIVATIVES

BACKGROUND OF THE INVENTION

1. Field of the Invention

This invention relates to polyfunctional hexasubstituted benzene derivatives and a method for making polyfunctional hexasubstituted benzene derivatives.

2. Description of the Related Art

Polyfunctional hexasubstituted benzene derivatives known in the art include hexacarboxymethylbenzene [Chem. and Ind., 239 (1964)], hexamethylolbenzene [U.S. Pat. No. 3,362,984], hexamethoxymethylenebenzene, hexa-(2-cyanoethoxy) methylenebenzene, hexaphenoxymethylenebenzene, hexatrimethylsilyloxymethylenebenzene [J. fur Prakt. Chemie 328 (1986)], and triphenyltricarboxybenzene [Chem. Ber., 93, 103 (1960)]. Polyfunctional hexasubstituted benzenes wherein at least 3 of the substituents are saturated carbon chains having 1 to 21 carbon atoms and having hetero functionalities at the end of the carbon chains have not been made.

The cyclotrimerization of simple alkynes to form benzene derivatives has been known in the art since 1866 when it was discovered that benzene can be formed in small amounts by high temperature treatment of acetylene [C. R. Hebd. Seances. Acad. Sci., 905 (1866)]. Over eighty years later, this same cyclization of acetylene to benzene was reported using a homogeneous nickel complex as a catalyst [Liebigs Ann. Chem., 560, 104 (1948)]. Since these original reports, a variety of transition metal complexes have been shown to catalyze the cyclotrimerization of alkynes to substituted benzene derivatives. Such cyclotrimerizations have been accomplished using such complexes as mercury, iron, cobalt, chromium, aluminum-titanium, nickel, palladium, tantalum, niobium, rhodium, ruthenium, and tungsten.

While many transition metals catalyze the reaction, many function only at stoichiometric levels, few provide good yields and even fewer provide good yields when applied to alkyne systems bearing large alkyl substituents. Many of these catalysts do not tolerate polar functional groups such as carboxylic acids, alcohols, and amines well. The only references [J. C. S. Dalton Trans., 2593 (1981) and Chem. Ber., 93, 103 (1960)] on the trimerization of alkynes possessing carboxylic acid functional groups describe conversions of only 11 to 14%. The selectivity of the reaction towards trimerization can also be low, producing linear polymers, tetramers, dimers, as well as several other monomeric and oligomeric by-products.

The use of palladium chloride complexes to catalyze the trimerization of acetylenic hydrocarbons is known [J. Am. Chem. Soc., 92, 2276 (1970)]. A particularly useful catalyst for this reaction is bis(benzonitrile)palladium chloride in a chlorocarbon solvent. This catalyst has been used in the cyclotrimerization of diphenylacetylene, methyl phenylacetylene and 2-butyne. Dimethyl acetylenedicarboxylate has been cyclotrimerized over palladium(0)-on-carbon to give the corresponding hexacarboxymethyl benzene (Chem. and Ind. 239 (1964). A homogeneous palladium chloride catalyst generated from palladium-on-carbon with trimethylsilyl chloride has been used to cyclotrimerize 3-hexyne and 4-decyne [J. Org. Chem., 52, 1161 (1987)].

SUMMARY OF THE INVENTION

It is an object of the present invention to provide polyfunctional hexasubstituted benzenes useful as metal complexing agents wherein at least three of the substituents are saturated carbon chains having from 1 to 21 carbon atoms and the functional groups are hetero functionalities at the end of the carbon chains of the formula I and II

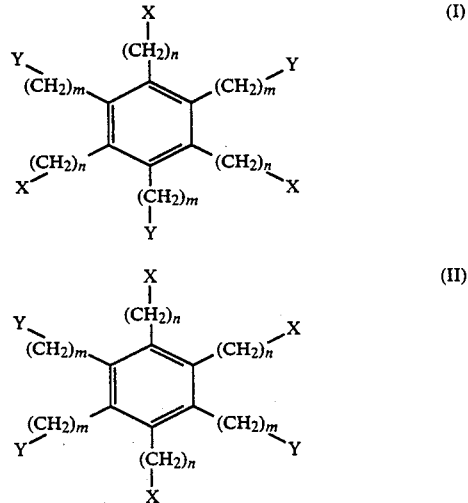

wherein each of X and Y is independently selected from the group consisting of $CH_3$, F, Cl, Br, I, and functional groups having N, O, S, P, or Si as hetero atom, with the proviso that X and Y are not both $CH_3$; each of m and n is an integer having a value of from 0 to 20, such that $m+n=2$ to 20, and when $X=Y$, $m+n=4$ to 20.

It is also an object of the present invention to provide a process for making compounds of formula I and II comprising (a) cyclotrimerizing a disubstituted alkyne wherein one or both of the substituents is a saturated carbon chain having from 1 to 21 carbon atoms and having a functional group having N, O, S, P, or Si as a hetero atom with a catalyst effective amount of palladium catalyst in an inert solvent for a period of time sufficient to form a reaction product, and (b) separating said reaction product from said catalyst.

DESCRIPTION OF THE PREFERRED EMBODIMENTS

The compounds of the present invention are hexasubstituted benzene derivatives useful as complexing agents for metal cations in aqueous media. At least 3 of the 6 substituents are saturated carbon chains containing from 1 to 21 carbon atoms having hetero functionalities at the end of the carbon chain. The remainder of the 6 substituents are either saturated carbon chains containing from 1 to 21 carbon atoms or saturated carbon chains containing from 1 to 21 carbon atoms and having hetero functionalities at the end of the chains. A hetero functionality is defined as a functional group having N, O, S, P, or Si bonded either directly to the end of the saturated carbon chain containing from 1 to 21 carbon atoms or bonded to a carbon atom which is directly bonded to the end of the saturated carbon chain containing from 1 to 21 carbon atoms.

Preferred examples of such functional groups having N, O, S, P, or Si hetero atoms include oxygen in a functional group such as alcohol, carboxyl, carboxylic ester, ether, ketone, and aldehyde; nitrogen in a functional group such as amide, amine, nitrile, imine, imide, and nitro; sulfur in a functional group such as sulfide, disulfide, sulfoxide, sulfone, sulfate ester, sulfonic acid, sulfonic acid ester and sulfonic acid amide; phosphorus in a functional group such as phosphine, phosphite, phosphinate, phosphonate, and phosphate; silicon in a functional group such as silane, siloxane, and silyl ether. The preferred functional groups are alcohol, acyloxy, carboxyl, and carboxylic esters wherein the R group of the ester moiety is an alkyl group having from 1 to 24 carbon atoms.

Any disubstituted alkyne wherein one or both of the substituents are saturated carbon chains having 1 to 21 carbon atoms to which functional groups as described above are bonded to the terminal carbons can be used to make the compounds of the present invention. Such alkynes are obviously those having an internal triple bond as opposed to alkynes having a terminal triple bond. Preferred disubstituted alkynes are fatty alkynes derivable from unsaturated fatty acids or derivatives of unsaturated fatty acids such as salts, esters, and amides. Fatty alcohols are also preferred. Such fatty acids include myristoleic, palmitoleic, oleic, and elaidic acids. Examples of fatty alcohols include myristoleyl, palmitoleyl, oleyl, and elaidyl alcohols.

The fatty alkynes used to make the compounds of the present invention can be made by any series of reactions generally known in the art for converting an alkene to an alkyne. The most preferred method is a method believed to be novel and inventive. It is carried out by first brominating an unsaturated fatty material to form a dibromo compound, completely dehydrohalogenating the dibromo compound to form an alkyne by contacting it with solid sodium hydroxide in the presence of a phase transfer catalyst. For example, neat oleyl alcohol is reacted with bromine at room temperature followed by the addition of 5-10% by weight of PEG (polyethylene glycol) 300 and powdered sodium hydroxide (2.5 equivalents based on oleyl alcohol taken), the resulting reaction mixture is heated to 120°-150° C. for 2-5 hours with vigorous stirring. The reaction mixture is then filtered to remove the solid sodium bromide and the remaining sodium hydroxide, and the filtrate phase separated to remove the PEG from the product. The alkynol product is then recovered by distillation. The resulting compound is a disubstituted alkyne wherein one substituent is a linear saturated carbon chain having 7 carbon atoms and having a alcohol functionality on the terminal carbon atom and the other substituent is a linear saturated carbon chain having 8 carbon atoms with no functional group on the terminal carbon atom. A similar series of reactions could be used with an olefinically unsaturated fatty acid, ester, amide, amine, or the like to produce the corresponding alkyne.

Compounds already containing an internal triple bond such as the naturally occurring alkynes tartaric, stearolic, and crepenynic acids can also be used to make the compounds of the present invention.

The compounds of the present invention are made by cyclotrimerizing any of the alkynes described by above by reacting the alkyne with a palladium(II) or palladium(0) catalyst in an inert solvent for a period of time sufficient to cyclotrimerize substantially all the alkyne to the corresponding hexasubstituted benzene derivative. The preferred method of making the compounds of the present invention is by contacting a disubstituted alkyne with bis(benzonitrile)palladium chloride in a chlorocarbon solvent such as methylene chloride for about 3 to about 24 hours depending upon the temperature of the reaction and the type of catalyst employed. For example, the reaction is continued for about 16 hours if it is carried out at room temperature in the presence of bis(benzonitrile)palladium chloride catalyst. On the other hand, the reaction is continued for about 3.5 hours if it is carried out at the boiling point of tetrahydrofuran (67° C.) in the presence of Pd/C catalyst which has been reacted with trimethylsilyl chloride. The reaction mixture is then heated to 180° C. to render the metal catalyst insoluble, and filtered through silica gel to remove the catalyst.

The cyclotrimerization process of the present invention produces a symmetrical benzene derivative when the alkyne is symmetrically disubstituted or a mixture of the symmetrical benzene derivative and the unsymmetrical benzene derivative when the disubstituted alkyne is substituted by 2 different substituents (asymmetrically substituted alkyne). For example, an alkyne of the type A—C≡C—B yields a mixture of products III (symmetric) and IV (unsymmetric) upon cyclotrimerization.

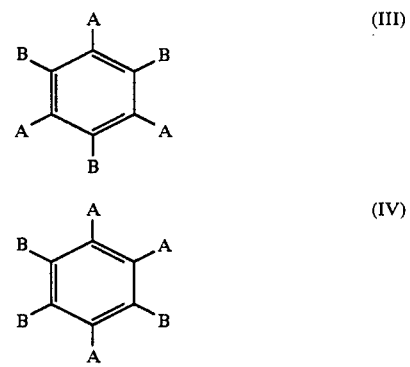

For purposes of this invention, it is understood that the terms symmetric and unsymmetric benzene derivatives refer to compounds like III and IV above.

The following examples are meant to illustrate but not limit the present invention.

EXAMPLE 1

Preparation of Trimer of 9-Octadecynoic Acid

9-Octadecynoic acid (70.8 g, 253 mmoles), was dissolved in dichloromethane (100 ml) and PdCl$_2$·(PhCN)$_2$ (1.79 g, 5.62 mmoles) added. The reaction was placed under a nitrogen atmosphere and the light orange reaction stirred overnight (ca. 20 hrs.) at room temperature. Thin layer chromatography indicated nearly total conversion of starting alkynyl acid to a new material of lower R$_f$. The solvent was removed by means of a roto-evaporator and the residue heated to 227° C. under a 0.5 torr vacuum to remove any unreacted monomer and precipitate the palladium present. This material was filtered through silica gel and the filter pad washed with ethyl acetate:hexane (2:1+2% acetic acid). Removal of solvent by means of a roto-evaporator yielded 69.5 g (98% yield) of a red-orange viscous material whose structure was confirmed by $^{13}$C and $^1$H NMR to be a mixture of two isomeric hexasubstituted aromatic triacids.

$^1$H NMR (200 MHz, CDCl$_3$): 2.47 ( m, 12 H), 2.35 (t, J=7.7 Hz, 6 H), 1.2-1.74 (m, 66H), 0.88 (m, 9 H). $^{13}$C

NMR (CDCl$_3$): 180.67, 180.67, 136.75, 136.71, 136.68, 136.57, 136.53, 136.49, 136.45, 34.11, 31.91, 31.45, 31.40, 31.34, 30.63, 30.35, 29.85, 29.74, 29.65, 29.29, 28.97, 24.66, 22.66, 14.08.

MS (NH$_3$-CI, %): 860 (M$^+$+2+NH$_4$, 19), 859 (M$^+$+1+NH$_4$, 46), 858 (M$^+$+NH$_4$, 100), 842 (M$^+$+2, 16), 841 (M$^+$+1, 49), 840 (M$^+$, 81), 404 (11), 390 (37), 387(11), 376 (17), 374 (12), 372 ( 14), 371 (13), 370 (24), 350 (12), 348 (29), 344 (27), 341 (13), 340 (13), 336 (39), 332 (13), 328 ( 12), 327 (13), 319 (11), 318 (41), 316 (47), 314 (15), 304 (30), 302 (12), 301 (16), 300 (56), 289 (30), 288 (76), 270 (16), 244 (11), 161 (14), 125 (12), 106 (13).

EXAMPLE 2

Preparation of Symmetric and Asymmetric tri-7-(carboxymethl)heptyl-tri-octylbenzene Methyl 9-octadecynoate (1.0 g, 88% pure by GC, 3.3 mmoles), was dissolved in dry tetrahydrofuran (4 mls) in a 25 ml round bottom flask under a nitrogen atmosphere. 10% palladium-on-activated carbon (0.25 g, Aldrich) was added followed by chlorotrimethylsilane (1 ml, Aldrich). The above reaction was heated to reflux for 3.5 hours. The reaction was cooled to room temperature and the solvent removed by way of a rotovap. Thin-layer chromatography indicated the presence a new product at lower R$_f$. Flash chromatography of this material produced 0.70 grams of a yellow viscous liquid which was structurally identified by $^1$H and $^{13}$C NMR to be a mixture of compounds two isomeric hexasubstituted aromatic triesters. Trace amounts of palladium were removed from the product by heating to 200 degrees C and filtering the material through silica gel. $^1$H NMR (200 MHz, CDCl$_3$): 3.65 (s, 9 H), 2.45 ( m, 12 H), 2.3 (t, J=7.3 Hz, 6 H), 1.10–1.75 (m, 66H), 0.87, (m, 9 H).

$^{13}$C NMR (CDCl$_3$): 174.07, 136.67, 136.64, 136.60, 136.57, 136.52, 136.48, 136.45, 136.40, 51.28, 33.98, 31.86, 31.41, 30.40, 29.68, 29.25, 29.10, 28.99, 24.88, 22.61, 14.03. MS (NH$_3$—Cl, %): 902 (M$^+$+2+NH$_4$, 17), 901 (M$^+$+1+NH$_4$, 75), 900 (M$^+$+NH$_4$, 100), 884 (M$^+$+2, 17.7), 883 (M$^{30}$+1, 43.6), 882 (M$^+$, 62.3), 483 (9.6), 439 (9.6), 401 (10.9), 389 (10), 387 (9), 385 (12), 384 (12), 369 (15), 355 (15), 353 (10),344 (10), 343 (9), 341 (23), 339 (9), 330 (10), 327 (15), 257 (10), 245 (13), 243 (11), 220 (10), 190 (40), 176 (21), 175 (18), 173 (15), 161 (16), 159 (13), 158 (10), 157 (49), 155 (69), 147 (13), 133 (11), 125 (26), 123 (16), 95 (18).

EXAMPLE 3

Preparation of Symmetric and Asymmetric tri-7-hydroxyoctyl-tri-octylbenzene

9-Octadecyn-1-ol (1 g, 3.7 mmoles), was dissolved in dichloromethane (5 ml). PdCl$_2$(PhCN)$_2$ (20 mg, 0.05 mmoles) was added and the reaction stirred overnight (ca. 20 hrs.) at room temperature. Thin layer chromatography indicated approximately 50% conversion of starting alkynol to a new material of lower R$_f$. The solvent was removed in vacuo and the unreacted 9-octadecyn-1-ol (450 mg) distilled off using a Kugelrohr distillation apparatus; palladium precipitated during this heating step. Flash chromatography (ether) of the residue yielded 200 mg of a yellow material whose structure was confirmed by $^{13}$C and $^1$H NMR to be a mixture of two isomeric hexasubstituted aromatic triols (see Example 4 for analysis of product).

EXAMPLE 4

Preparation of Symmetric and Asymmetric tri-7-hydroxyoctyl-tri-octylbenzene (by trimerization of 1-acetoxy-9-octadecyneand subsequent hydrolysis)

1-Acetoxy-9-octadecyne (69.1 g, 224 mmoles), was dissolved in dry tetrahydrofuran (200 mls) in a 500 ml round bottom flask under a nitrogen atmosphere. 10% Palladium on activated carbon (10 g, Aldrich) was added followed by chlorotrimethylsilane (60 ml, Aldrich). The above reaction was heated to reflux for 4 hours. The reaction was cooled to room temperature, filtered and the solvent removed by way of a rotoevaporator. Thin layer chromatography indicated near total consumption of starting alkyne and the presence a new product at lower R$_f$. The monomers were distilled off using a Kugelrohr distillation apparatus during which time much of the palladium catalyst plated out. Flash filtration through silica gel (hexane:ether 1:1) provided an orange viscous material (ca. 68 g, 98%). This material was treated with methanol (400 ml) and concentrated HCl (1 ml) and refluxed for a total of six hours. The methanol was removed in vacuo to yield a yellow viscous material (58 g) A portion of this material was re-chromatographed (hexane ether) to provide a pure sample. $^1$H and $^{13}$C NMR of this material indicated the presence of the same two isomeric hexasubstituted aromatic triols as were produced in Example 3.

$^1$H NMR (200 MHz, CDCl$_3$): 3.63 (t, J=6.49 Hz, 6H), 2.47, (m, 12 H), 1.0–1.6 (m, 72 H), 0.88 (m, 9 H). $^{13}$C NMR (CDCl$_3$): 136.55, 136.52, 136.50, 136.47, 136.45, 62.50, 62.44, 32.55, 31.81, 31.35, 30.51, 29.62, 29.37, 29.19, 25.70, 22.56, 13.99. MS (E.I, %): 800 (M$^+$+2,16%), 799 (M$^+$+1,46%),798 (M$^+$, 100), 71 (11), 69 ( 24), 57 (26), 55 (25).

EXAMPLE 5

Preparation of symmetric and asymmetric tri-4-(carboxymethyl)butyl-tri-undecylbenzene Methyl 6-Octadecynoate (1.1 g, 3.3 mmoles), was dissolved in dichloromethane (20 ml). PdCl$_2$(PhCN)$_2$(20 mg, 0.05 mmoles) was added and the reaction stirred overnight (ca. 20 hrs) at room temperature. Thin layer chromatography indicated high conversion of starting alkynyl ester to a new material of lower R$_f$. The solvent was evaporated under vacuum and the material submitted to flash chromatography (hexane : ether 5:1) to yield 714 mg of an orange viscous material whose structure was confirmed by $^{13}$C and $^1$H NMR to be a mixture of two isomeric hexasubstituted aromatic triesters.

$^1$NMR (200 MHz, CDCl$_3$): 3.65 (s, 9 H), 2.2–2.55 (m, 18 H), 1.1–1.9 (m, 66 H), 0.86 (m, 9 H). $^{13}$C NMR (CDCl$_3$): 174.12, 173.93, 136.90, 136.78, 136.74, 136.62, 136.16, 136.06, 135.99, 135.89, 51.38, 34.22, 33.98, 33.76, 31.83, 31.51, 31.44, 31.08, 30.97, 30.55, 30.40, 29.58, 29.46, 29.29, 29.09, 28.97, 25.80, 24.86, 22.61, 19.05, 14.42, 13.62. MS (E.I., %): 884 (M$^+$+2, 11), 883 (M$^+$+1, 34) 882 (M$^+$, 69), 116 (7), 115 (100).

EXAMPLE 6

Trimerization of 16-Octadecynoic Acid

16-Octadecynoic acid (26.1 g, 93 mmoles), was dissolved in dichloromethane (26 ml) and chloroform (10 ml). PdCl$_2$(PhCN)$_2$ (1.79 mg, 5.62 mmoles) was added and the reaction placed under a nitrogen atmosphere.

The light orange reaction was stirred overnight (ca. 20 hrs.) at room temperature. Thin layer chromatography indicated nearly total conversion of starting alkynyl acid to a new material of lower $R_f$. The solvent was removed by means of a roto-evaporator and the residue heated to 227° C. under a 0.5 torr vacuum to remove any unreacted monomer and precipitate the palladium present. This material was filtered through silica gel and the filter pad washed with ethyl acetate : hexane (2:1+2% acetic acid).

Removal of solvent by means of a roto-evaporator yielded 16.1 g of a red-orange viscous material whose structure was confirmed by $^{13}C$ and $^{1}H$ NMR to be a mixture of two isomeric hexasubstituted aromatic triacids.

What is claimed is:

1. A composition selected from the group consisting a compound of the formula I or II

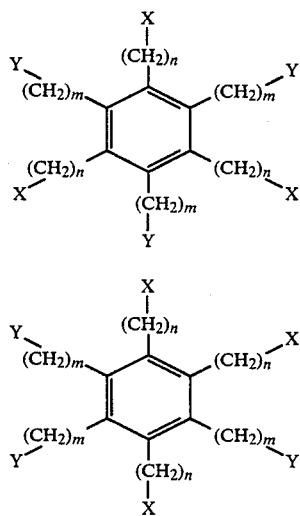

wherein each of X and Y is independently selected from the group consisting of $CH_3$, F, Cl, Br, I, and functional groups having N, O, S, P, or Si as hetero atom, with the proviso that X and Y are not both $CH_3$; each of m and n is an integer having a value of from 0 to 20, such that m+n=2 to 20, and when X=Y, m+n=4 to 20.

2. A compound of claim 1 wherein X is OH, Y is $CH_3$, m is 14 and n is 1.

3. A compound of claim 1 wherein X is $CO_2H$, Y is $CH_3$, m is 14 and n is 0.

4. A compound of claim 1 wherein X is $CO_2CH_3$, Y is $CH_3$, m is 14 and n is 0.

5. A compound of claim 1 wherein X is OH, Y is $CH_3$, m is 10 and n is 5.

6. A compound of claim 1 wherein X is $CO_2H$, Y is $CH_3$, m is 10 and n is 4.

7. A compound of claim 1 wherein X is $CO_2CH_3$, Y is $CH_3$, m is 10 and n is 4.

8. A compound of claim 1 wherein X is OH, Y is $CH_3$, m is 7 and n is 8.

9. A compound of claim 1 wherein X is $CO_2H$, Y is $CH_3$, m is 7 and n is 7.

10. A compound of claim 1 wherein X is $CO_2CH_3$, Y is $CH_3$, m is 7 and n is 7.

11. A compound of claim 1 wherein X is OH, Y is $CH_3$, m is 0 and n is 15.

12. A compound of claim 1 wherein X is $CO_2H$, Y is $CH_3$, m is 0 and n is 14.

13. A compound of claim 1 wherein X is $CO_2CH_3$, Y is $CH_3$, m is 0 and n is 14.

14. A compound of claim 1 wherein X is $OC(O)CH_3$, Y is $CH_3$, m is 0 and n is 15.

15. A compound of claim 1 wherein X is OH, Y is OH, m is 8 and n is 8.

16. A compound of claim 1 wherein X is $CO_2H$, Y is $CO_2H$, m is 7 and n is 7.

17. A compound of claim 1 wherein X is $CO_2CH_3$, Y is $CO_2CH_3$, m is 7 and n is 7.

18. A compound of claim 1 wherein X is OH, Y is $CH_3$, m is 0 and n is 2.

19. A compound of claim 1 wherein X is $CO_2H$, Y is $CH_3$, m is 0 and n is 2.

20. A compound of claim 1 wherein X is $CO_2CH_3$, Y is $CH_3$, m is 0 and n is 2.

21. A compound of claim 1 wherein X is $CO_2CH_2CH_3$, Y is $CH_3$, m is 0 and n is 2.

22. A compound of claim 1 wherein X is OH, Y is OH, m is 2 and n is 2.

23. A compound of claim 1 wherein X is $CO_2H$, Y is $CO_2H$, m is 2 and n is 2.

24. A compound of claim 1 wherein X is $CO_2CH_3$, Y is $CO_2CH_3$, m is 2 and n is 2.

25. A compound of claim 1 wherein X is $CO_2CH_2CH_3$, Y is $CO_2CH_2CH_3$, m is 2 and n is 2.

26. A process for making a compound of claim 1 comprising the steps of: (a) contacting a disubstituted alkyne wherein one or both of the substituents is a saturated carbon chain having from 1 to 21 carbon atoms and having a functional group bonded to the terminal carbon atom of said carbon chain wherein said functional group has a hetero atom selected from the group consisting of N, O, S, P, or Si with a catalyst effective amount of palladium catalyst in an inert solvent for a period of time sufficient to form a reaction product, and (b) separating said reaction product from said catalyst.

27. The process of claim 26 wherein said catalyst is 5% palladium-on-carbon reacted with trimethylsilyl chloride.

28. The process of claim 26 wherein said catalyst is bis(benzonitrile)palladium chloride.

29. The process of claim 26 wherein said inert solvent is dichloromethane.

30. The process of claim 26 wherein said inert solvent is tetrahydrofuran.

31. The process of claim 26 wherein said contacting step (a) is carried out at a temperature of from about 20° C. to about 100° C.

* * * * *